United States Patent [19]

Igaue et al.

[11] Patent Number: 5,788,663

[45] Date of Patent: Aug. 4, 1998

[54] SANITARY TAMPON APPLICATOR

[75] Inventors: Takamitsu Igaue; Masaki Murakami, both of Ehime-ken; Shingo Shimizu, Kagawa-ken, all of Japan

[73] Assignee: UNI-Charm Corporation, Ehime-ken, Japan

[21] Appl. No.: 543,459

[22] Filed: Oct. 16, 1995

[30] Foreign Application Priority Data

Oct. 21, 1994 [JP] Japan .................................. 6-256675

[51] Int. Cl.$^6$ .................................................. A61F 13/20
[52] U.S. Cl. ............................. 604/15; 604/904; 604/11
[58] Field of Search ............................... 604/11–18, 904, 604/285

[56] References Cited

U.S. PATENT DOCUMENTS

| | | | |
|---|---|---|---|
| 3,424,158 | 1/1969 | Silver | 604/285 |
| 4,060,083 | 11/1977 | Hanson | 604/285 |
| 4,198,978 | 4/1980 | Nigro | 604/14 |
| 4,620,534 | 11/1986 | Zartman | 604/14 |
| 4,895,559 | 1/1990 | Shippert | 604/15 |

FOREIGN PATENT DOCUMENTS 63-48261   12/1988   Japan .

*Primary Examiner*—John G. Weiss
*Assistant Examiner*—Dennis Ruhl
*Attorney, Agent, or Firm*—Lowe, Hauptman, Gopstein, Gilman & Berner

[57] ABSTRACT

A sanitary tampon applicator includes an outer cylinder around which there is provided a stopper having differently dimensioned vertical and horizontal extents. The stopper is tilted rearward at a desired angle along the vertical extent thereof.

5 Claims, 2 Drawing Sheets

SANITARY TAMPON APPLICATOR

BACKGROUND OF THE INVENTION

The present invention relates to a sanitary tampon applicator, and more particularly, to an applicator used to insert a sanitary tampon into a woman's vagina.

A sanitary tampon applicator provided with a collar-like stopper extending radially outward from a peripheral surface of the applicator is disclosed in Japanese Utility Model Application Publication No. Sho 63-48261.

The stopper certainly prevents the applicator from being inserted into the vagina to an excessively deep extent and at the same time prevents the user's fingers from being smeared with menstrual discharge by holding the applicator behind the stopper. However, the known applicator has its diameter enlarged by the presence of the stopper and cannot meet the user's demand that a sanitary tampon including the applicator be packaged in a minimum size so as to be easily carried.

Obviously, the applicator must be inserted into the vagina with its forward end directed obliquely upward. However, a user having no experience with use of this type of applicator often thrust the tampon in an improper direction and fails to insert the tampon into the vagina. In consequence, the tampon must be wastefully disposed of.

SUMMARY OF THE INVENTION

Accordingly, it is a principal object of the invention to solve the above-mentioned problem by dimensioning a stopper provided around an outer cylinder smaller in the transversal direction than in the vertical direction so that a package size thereof may be minimized, on one hand, and by tilting the vertical direction of the stopper with respect to a longitudinal axis of the applicator so that the applicator may be spontaneously held so as to be directed obliquely upward, on the other hand.

The object set forth above is achieved, according to the invention, by a sanitary tampon applicator comprising an outer cylinder, an inner cylinder for pushing out a tampon contained within the outer cylinder from a forward end of the outer cylinder, and a stopper extending radially outward from a peripheral surface of the outer cylinder. The stopper is provided with a means for allowing the radially vertical extent and the radially horizontal extent of the stopper to be distinguished from each other.

Preferably, the distinguishing means comprises dimensioning the horizontal extent of the stopper to be significantly smaller than its vertical extent. In another preferred embodiment, the means comprises tilting the vertical extent of the stopper rearward at a desired angle with respect to a longitudinal axis of the applicator.

The applicator arranged as described above allows its package size to be reduced by the reduced horizontal extent of the stopper relative to its vertical extent. When the applicator is inserted into the vagina, the fingers holding the applicator may be placed against the rear side of the stopper vertical extent to ensure that the applicator may be spontaneously directed obliquely upward and easily inserted into the vagina.

PREFERRED EMBODIMENTS OF THE INVENTION

Details of a sanitary tampon applicator according to the invention will be readily understood from the following description made in reference with the accompanying drawings.

Figure 1:
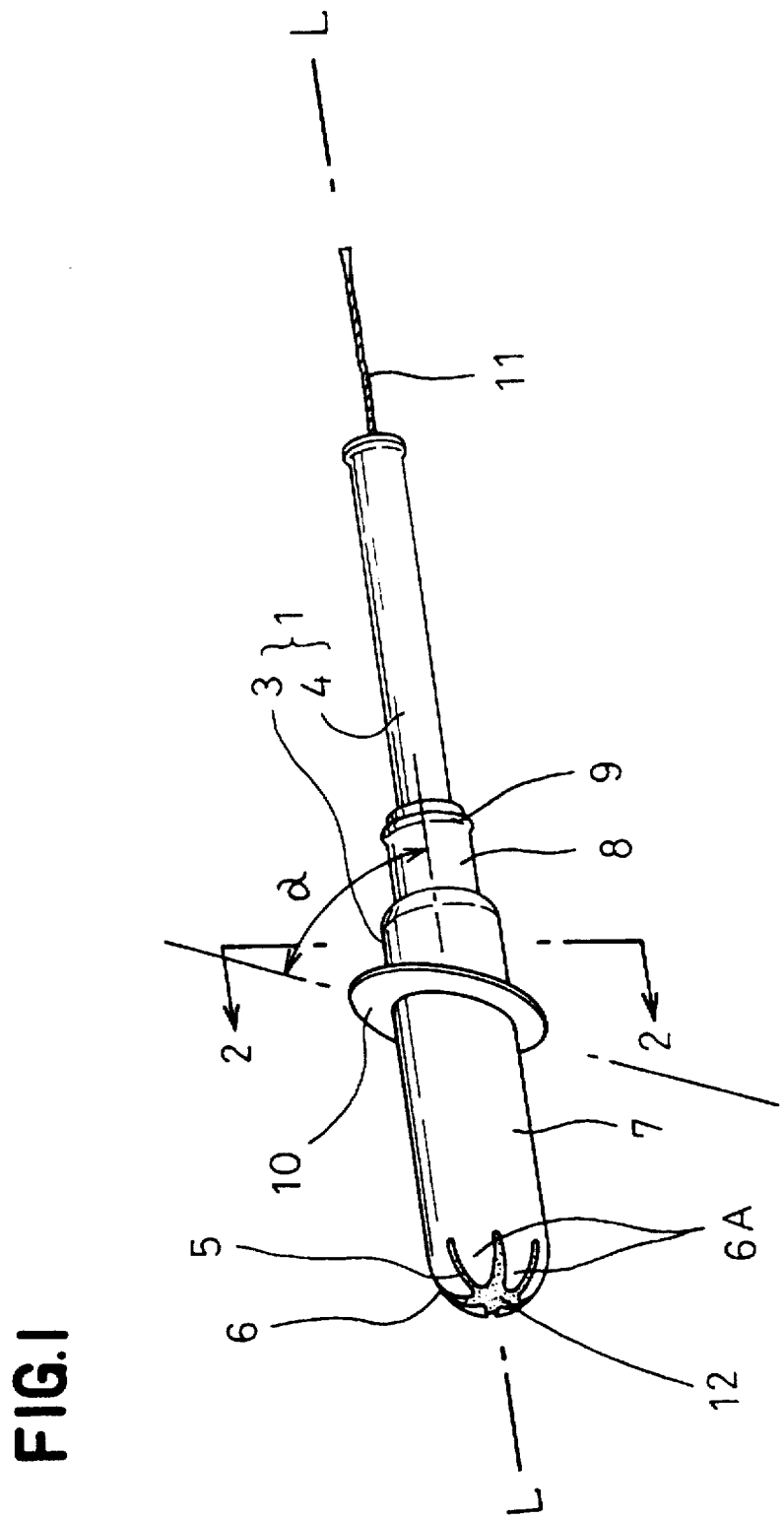
FIG. 1 is a perspective view of a sanitary tampon applicator of the invention.
Figure 2:
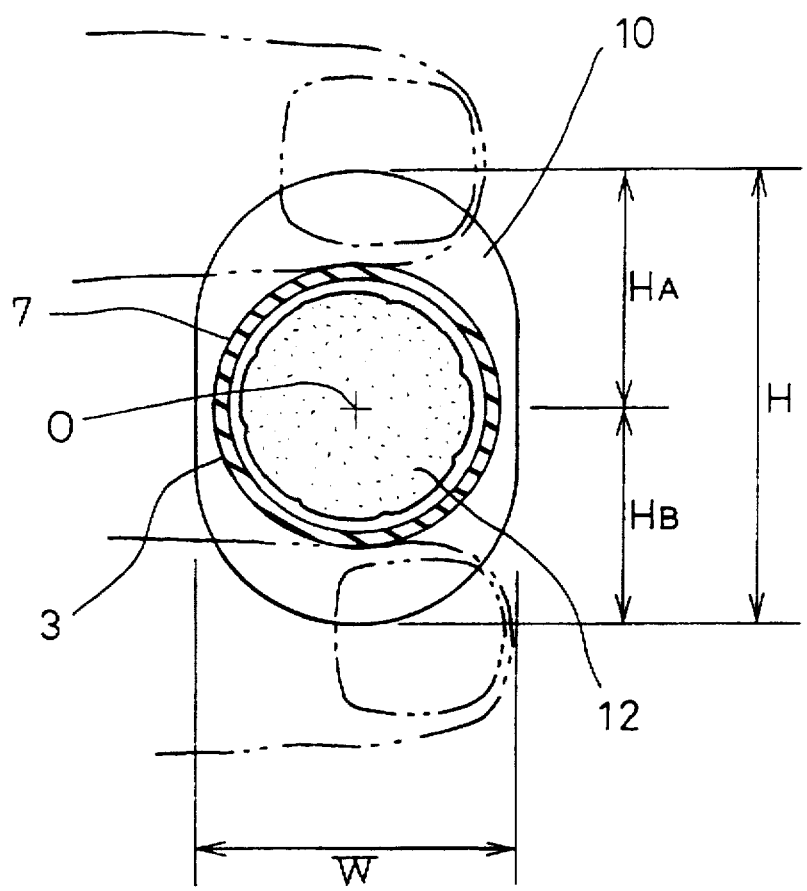
FIG. 2 is a sectional view taken along the line 2—2 in FIG. 1.

Referring to FIGS. 1 and 2, the sanitary tampon applicator 1 comprises an outer cylinder 3 and an inner cylinder 4 made from plastics, respectively. The outer cylinder 3 comprises an enlarged diameter portion 7 provided with a substantially semispherical forward end 6 which is split by means of a plurality of slits 5 into a plurality of triangular petals 6A, a reduced diameter portion 8 provided around its rear end with a rib 9, and a flange-like stopper 10 integrally provided around the enlarged diameter portion 7 adjacent the reduced diameter portion 8. The outer cylinder 3 contains therein a tampon 12 compression-molded from hydrophilic fibers and having a pull cord attached thereto. The inner cylinder 4 is adapted to be slidably inserted into the outer cylinder 3 until its forward end (not shown) comes in contact with a rear end of the tampon 12 with the pull cord 11 extending from the rear end. In use, a rear end of the tampon 12 is engaged by the inner cylinder 4 to force open the respective petals 6A. In consequence, the tampon 12 is pushed out from the forward end of the outer cylinder 3.

The stopper 10 is molded integrally with the enlarged diameter portion 7 having a total height of $H=H_A+H_B$, where $H_A$ and $H_B$ represent dimensions as measured upward and downward from a center "0" in a cross-section of the enlarged diameter portion 7, and a width "W". The total height "H" is larger than the width "W". $H_A$ and $H_B$ extend outward from the peripheral surface of the enlarged diameter portion 7 by 3 to 10 mm and preferably $H_A \geq H_B$. The width "W" may be dimensioned to be equal to an outer diameter of the diameter portion 7, if it is desired. A vertical extent of the stopper 10 is preferably tilted toward the rear end of the applicator 1A at an angle $\alpha=80$ to $60°$ with respect to a longitudinal axis L—L of the enlarged diameter portion 7.

To insert the applicator 1 into the vaginal opening, the user may hold the diameter enlarged portion 7 with the finger tips from above and below, for example, as illustrated by imaginary lines in FIG. 2. If the user places the pair of finger tips against the rear side of the stopper 10, the applicator 1 will be almost spontaneously directed obliquely upward and a smooth insertion will be assured even for the user having no experience with use of such an applicator. Shortly after the insertion has been begun, the tilted stopper 10 bears against spots of the user's body extending immediately above and below the vaginal opening and the user can reliably detect when the applicator 1 has been properly inserted into the vaginal opening. The stopper 10 also functions to obstruct possible flow back of menstrual discharge. Furthermore, the width "W" of the stopper 10 having practically no contribution to protect the user's skin against smear with menstrual discharge is minimized without excessively enlarging the outer diameter of the applicator 1, so the applicator 1 can be compactly packaged.

The sanitary tampon applicator of the invention is advantageous in that the vertical direction and horizontal direction of the stopper can be distinguished from each other when the user pinches the applicator. The stopper is dimensioned to be larger in its vertical direction than in its horizontal direction in order to prevent the user's finger tips from being smeared with menstrual discharge during insertion of the applicator. The vertical direction of the stopper is tilted rearward so that the applicator may be spontaneously directed obliquely upward and a smooth insertion may be assured even for the user having no experience of using such applicator. The stopper is dimensioned to be relatively narrow transversely thereof, so the applicator containing the tampon as a whole becomes correspondingly compact to be packaged as well as to be carried.

What is claimed is:

1. A sanitary tampon applicator in combination with a tampon, comprising said applicator including an outer cylinder, said tampon contained within said outer cylinder, an inner cylinder movably disposed within said outer cylinder to push out the tampon contained within said outer cylinder from a forward end thereof, and a stopper extending radially outward from a peripheral surface of said outer cylinder, wherein said stopper is tilted at a non-orthogonal angle relative to a longitudinal axis of said applicator.

2. The sanitary tampon applicator according to claim 1, wherein said stopper includes a horizontal extent of said stopper being smaller than a vertical extent thereof.

3. A sanitary tampon applicator according to claim 1, said stopper being tilted rearward in a vertical direction at a desired angle with respect to a longitudinal axis of said applicator.

4. The sanitary tampon applicator of claim 1, wherein said stopper is tilted at an angle of 60°–80° with respect to said longitudinal axis.

5. A sanitary tampon applicator in combination with a tampon, comprising said applicator including an outer cylinder, said tampon contained within said outer cylinder, an inner cylinder movably disposed within said outer cylinder to push out the tampon contained within said outer cylinder from a forward end thereof, and a stopper extending radially outward from a peripheral surface of said outer cylinder, wherein said stopper includes a means for distinguishing a radially vertical extent from a radially horizontal extent of said stopper through a user's touching of the stopper, wherein said distinguishing means includes said stopper being tilted rearward in a vertical direction at a desired angle with respect to a longitudinal axis of said applicator.

* * * * *